United States Patent [19]

Danna et al.

[11] Patent Number: 5,278,642
[45] Date of Patent: Jan. 11, 1994

[54] COLOR IMAGING SYSTEM

[75] Inventors: Dominick A. Danna, Syracase; Raymond A. Lia, Auburn; William R. Miller, Skaneateles Falls; Richard W. Newman, Auburn; Teresa M. West, Skaneateles Falls, all of N.Y.

[73] Assignee: Welch Allyn, Inc., Skaneateles Falls, N.Y.

[21] Appl. No.: 841,570

[22] Filed: Feb. 26, 1992

[51] Int. Cl.⁵ .............................................. H04N 7/18
[52] U.S. Cl. ........................................ 358/98; 128/4; 358/55
[58] Field of Search ....................... 358/98, 41, 42, 44, 358/55, 58, 49, 50, 100; 128/4, 6; 356/241; H04N 7/18

[56] References Cited

U.S. PATENT DOCUMENTS

| 2,929,866 | 3/1960 | Meland | 358/49 |
| 4,879,592 | 11/1989 | Ernest | 358/42 |
| 5,155,585 | 10/1992 | Ishikawa | 358/42 |
| 5,222,477 | 6/1993 | Lin | 358/98 |

Primary Examiner—Mark R. Powell
Assistant Examiner—Michael H. Lee
Attorney, Agent, or Firm—Wall and Roehrig

[57] ABSTRACT

A color camera employs a monochrome imager and a color filter plate that is divided into a plurality of primary color filter sections. The filter sections can be individually shuttered electronically for transmitting color sequential images onto the imager. In one embodiment there are red, blue, and green color filter sectors that radiate from a center at the optic axis of the camera. In an alternative embodiment, concentric annular color filters are provided.

11 Claims, 1 Drawing Sheet

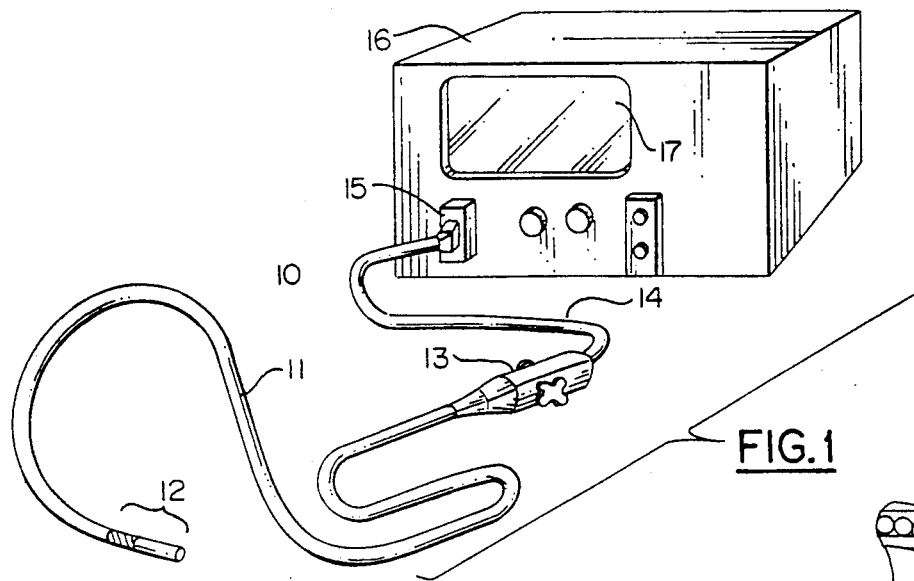
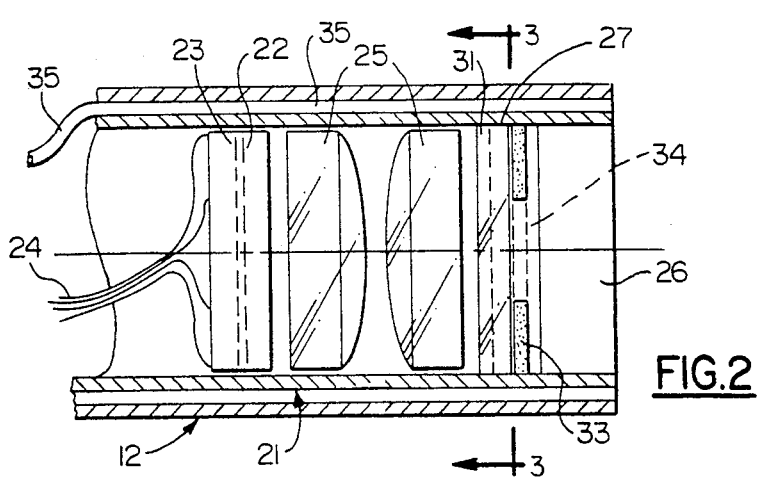
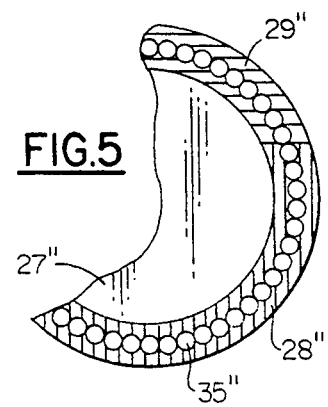
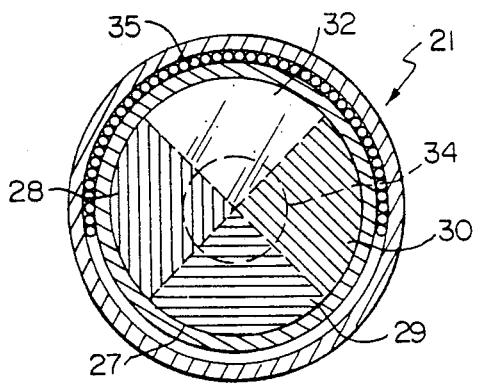
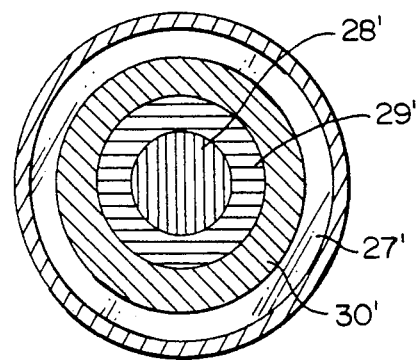
FIG.1
FIG.5
FIG.2
FIG.3
FIG.4

COLOR IMAGING SYSTEM

BACKGROUND OF THE INVENTION

This invention relates to color video cameras, and in particular to those employed in confined spaces, such as in borescopes or endoscopes of the type in which a miniature video camera is mounted at a distal viewing head of an elongated insertion tube. The invention is more specifically concerned with an arrangement of the miniature video camera which produces color video images using a single monochrome video imaging device combined with a controllable color filter assembly.

Recently, interest has increased in the use of video instruments for surgical applications to permit a surgeon to carry out a procedure with minimal intervention in the patient. An example of one such video instrument is a laparoscope for performing surgery in the abdominal cavity, where the instrument is inserted through a small incision. There is also an increased interest in remote imaging of industrial processes, such as inspection of heat exchanger tubes or of turbine engines, where remote color imaging could be employed to advantage.

However, in current imaging systems, either a complex and expensive color imaging CCD type device is employed or else color sequential illumination is provided to produce red, blue, and green illumination in turn onto the target of the camera or imaging assembly.

Full-color video borescopes and endoscopes are well known, and have been described, for example, in Danna et al. U.S. Pat. No. 4,491,365, Danna et al. U.S. Pat. No. 4,539,586, and Longacre et al. U.S. Pat. No. 4,523,224. The latter describes a colorsequential system in which sequential primary color light is supplied over a fiber optic bundle to illuminate the target area sequentially with primary color light. With the present systems a white illumination source is sequentially pulsed to produce red, green and blue light that is then carried over a fiber optic bundle to the probe tip. The illumination is pulsed mechanically using a chopper wheel or filter wheel which must be synchronized with the display electronics. This filter wheel is big, slow to synchronize, mechanically complex and expensive. The systems of this type require a built-in light source and cannot be made to produce a color image with ambient light.

OBJECT AND SUMMARY OF THE INVENTION

Accordingly, it is an object of this invention to provide a simple and efficient color imaging camera system for a borescope or endoscope, using either ambient light or a light from a light source.

It is another object of this invention to provide a color imaging system for a borescope or endoscope in which a monochrome CCD or other imaging system, which could alternatively include a fiber-optic bundle or relay lens system, provides a sequence of primary color images, with white light being employed to illuminate the target.

It is a further object of this invention to provide a color sequential imaging system that is small, has no moving parts, and produces excellent color images using a black-and-white camera or imager device.

In accordance with one aspect of this invention, a miniature camera assembly, which is disposed at the distal tip of a probe, such as a borescope or endoscope insertion tube, includes a CCD imager or the like, a focusing lens assembly for focusing on the image plane of the imager an image of a target in the viewing field of a camera assembly, and a filter plate that is interposed in the optical path of the camera assembly adjacent the lens assembly. The filter plate is provided with primary color filter in respective sectors or zones. These sectors can be situated symmetrically about the optic axis of the lens assembly. The three primary color images pass through the respective sectors, in turn, and are focused by corresponding portions of the lens assembly onto the image plane. A filter selecting device, such as a set of alternately opening shutters, permits the red, blue and green images to be formed in turn to produce a color sequential video signal. This is then employed to generate a full color image of the target. Alternatively, color filters could be employed over concentric annular zones. As a further alternative, if the imager includes a coherent fiber-optic bundle rather than a solid-state or CCD imager, the color viewing system could include a monochrome camera at the proximal or viewing and of the probe, with the filter plate being disposed either at the viewing tip or at the camera.

With this system, ambient light can be employed, thus avoiding the need for sequential color illumination. Illumination over a range of color temperatures can be employed, as the duty cycle of each of the primary color filters can be controlled to produce a color-balanced signal. With the system of this invention, manufacturing is made as simple and cost effective as possible.

The above and many other objects, features, and advantages of this invention will become more fully appreciated from the ensuing description of a preferred embodiment, which should be read in connection with the accompanying Drawing.

BRIEF DESCRIPTION OF THE DRAWING

FIG. 1 is a perspective view of an endoscope or borescope according to one embodiment of this invention.

FIGS. 2 and 3 are a top section and a front view of a camera assembly, illustrating one embodiment.

FIG. 4 is a front view of an alternative embodiment of this invention.

FIG. 5 is a front view of a further embodiment of this invention.

DETAILED DESCRIPTION OF THE PREFERRED EMBODIMENT

With reference to the Drawing, FIG. 1 shows a video borescope or endoscope assembly 10, in this case having an elongated, flexible insertion tube 11 with a viewing head 12 situated at its distal tip. In other embodiments, the probe could be a hard, rigid tube. The viewing head contains optical lenses and a miniature camera to be described below. At the proximal end of the insertion tube 11 is a steering and control unit 13 which couples the insertion tube to a flexible umbilical or tubular extension 14. At the proximal end of the umbilical 14 is an interface module or connector 15 of the plug-in type, for example, as disclosed in U.S. Pat. No. 4,539,586. The connector module 15 fits a mating receptacle in a video processor 16. Included in the processor 16 is a video monitor screen 17, which can be, e.g. a color CRT monitor, a liquid crystal display, or another other suitable display device. The process 16 can contain data memory for storing one or more video images.

As mentioned above, within the distal tip 12 of the endoscope or borescope insertion tube there is a miniature camera 21, as described here and as shown, e.g. in FIGS. 2 and 3. In this embodiment, the camera 21 contains a CCD imager 22 which has an image plane 23 on which there are an array of pixels. In this embodiment, the imager 22 is a monochrome device. A conductor bundle 24 or wiring harness carries the video signal back through the insertion tube 11 to the video processor 16.

As mentioned previously, rather than a solid state electronic device, the imager 22 can take the form of a coherent fiber optic bundle in which the image is conveyed over a multitude of optical fibers back to a not-shown camera or viewing device at the proximal end of the tube 11. Devices of this type are often referred to as fiberscopes.

Also in the miniature camera 21 is a focusing lens assembly 25 which acquires the image of a target in the viewing field of the camera and focuses the image onto the image plane 23. In this case, a wide-angle lens assembly 25 is employed having a large effective aperture, typically f/2 or wider. However, the lens can be used over a wide range of f numbers. A transparent face plate 26 is disposed at the distal end of the camera 21 and includes means to seal the camera from environmental fluids.

Color imaging is achieved with a filter plate 27 which is interposed in the optical path of the camera adjacent the lens assembly 25. Depending on the nature of the lens elements employed, the filter plate 27 can be disposed between the lens elements as shown here, or in advance thereof, or behind the lens elements. As shown in FIG. 3, the filter plate 27 has formed therein a red filter 28, a blue filter 29, and a green filter 30, each in the form of a sector of the plate 27, radiating from the center, at which the optic axis of the lenses 25 is found. A shutter assembly 31 is disposed adjacent the filter plate, and here has respective shutter means which open in succession. The shutter assembly is synchronized and controlled from the video processor 16, such that the light is transmitted through the red, blue and green filters in turn, to form color sequential images of the target on the image plane 23 of the imager 22. Alternatively, other wavelengths such as IR, UV, or a specific visible wavelength could be used for imaging. In one preferred mode, liquid crystal shutters are employed as the shutter assembly 31, although other shutters or other known systems could be used. In the present embodiment there is fourth, clear sector 32 provided on the plate 27 which can be employed for monochrome imaging. In other embodiments the clear sector can be omitted. As further shown in FIG. 2, there is an electronically controllable aperture plate 33 disposed adjacent the filter plate 27 in the optical path of the camera 21. This plate 33 is also controllable from the processor 16 to control an effective pupil 34 thereof to match existing light conditions.

Another embodiment of the camera 21 is shown in FIG. 4, in which similar elements are identified with the same reference numbers as used previously, but primed. In this embodiment, the filter plate 27' has a series of concentric annular zones on which are formed the red, blue, and green filters 28', 29', 30'. These are centered on the camera optic axis. The associated shutter plate has matching concentric shutter zones, which are actuated selectively.

Returning now to FIGS. 2 and 3, a fiber optic bundle 35 brings white light illumination from the video processor 16 and has its distal end fanned out in an arc at the distal end of the camera assembly 21. The color temperature of the illumination can be controlled, if desired, by employing suitable filters at the source of illumination. However, the color balance of the color sequential video signal can also be easily controlled by adjusting the shutter times, i.e., the respective duty cycles, of the shutters associated with the red, blue, and green filters 28, 29, 30. This also permits the arrangement of this invention to be used to advantage with ambient light or with an arbitrary light source. The shutter times can also be adjusted to control exposure times, or to adjust the relative areas of red, blue, and green filters through which the light passes.

In still other embodiments, other colors of light filters, including ultraviolet or infrared, can be employed, for instance, for fluorescent penetrant inspection, infrared, ultraviolet, or medical image highlighting.

FIG. 5 illustrates a portion of another embodiment in which a filter plate 27" disposed on a front face of the camera has a blue filter portion 28" and a red filter portion 29" each covering a respective segment of the annular array of light-emitting optical fibers 35". A green filter portion is omitted from this view. In this case a central part of the plate 27" can be clear.

There may be multiple filter zones or different size filter zones or apertures for the color filters, to balance or emphasize the resolution and illumination levels for each primary color depending on the sensitivity of the imager. This system can also be arranged to provide one-camera stereo imaging, by capturing two images alternatively through opposite halves of the focussing lenses.

The color imaging system of this invention can operate with standard light source boxes or in ambient light, and the color feature can be selected electronically with no moving parts. The cost of the black and white imager is significantly less than the cost of a color imager, while the pixel unit density of the monochrome imager can be much higher.

The term imager as used herein comprehends not only a video type device, but also for example silver halide based film on which a latent image can be stored and developed.

While this invention has been described in detail with respect to certain preferred embodiments, it should be understood that the invention is not limited to those precise embodiments. Rather, many modifications and variations would present themselves to those of skill in the art without departing from the scope and spirit of this invention, as defined in the appended claims.

What is claimed is:

1. A color imaging and viewing system for borescope or endoscope, comprising a camera assembly that includes an imager having an image plane, a focusing lens assembly for focusing on the imager an image of a target in the viewing field of said camera assembly, a stationary filter plate fixedly interposed in the optical path of said camera assembly adjacent to said lens assembly, having a plurality of primary color filter means therein situated in respective zones of the filter plate, and selective means for selectively shuttering said color filter means in turn to pass respective color images of the target onto said imager to produce a color sequential color video signal.

2. A color imaging system according to claim 1 wherein said primary filter means includes red, green, and blue filters formed as respective sectors, each radiating out from the optic axis of said lens assembly.

3. A color imaging system according to claim 2, wherein said color filter plate also includes a clear sector radiating from the optic axis.

4. A color imaging system according to claim 1, wherein said filter means includes red, green, and blue filters formed as respective concentric annular zones centered on the optic axis of said lens assembly.

5. A color imaging system according to claim 1, further comprising viewing means coupled to said imager to receive said color sequential video signal therefrom and visually display a full color view of the target.

6. A color imaging system according to claim 1, further comprising storage means coupled to said imager to receive said color sequential video signal therefrom and store therein a full color view of the target.

7. A color imaging system according to claim 1, wherein said filter plate has red, green, and blue filters formed thereon as respective concentric annular zones centered on the optic axis of said lens assembly.

8. A color imaging system according to claim 1 further comprising an aperture plate disposed adjacent said lens assembly for controlling the effective apperture of said lens assembly.

9. A color imaging system according to claim 1 wherein said selective means includes electronically controllable shutter devices disposed adjacent said primary color filter means.

10. A color imaging system according to claim 9 wherein said electronically controllable shutter devices includes liquid crystal shutters.

11. An illuminating and imaging camera system comprising a camera assembly that includes an imager having an image plane, a focusing lens assembly for focusing on the imager plane of said imager an image of a target in the viewing field of said camera assembly, an illuminating conduit carrying illumination forward and emitting light from said camera system onto said target, a stationary filter fixedly disposed in the path of the light emitted from said conduit and having primary color filter means therein situated in respective zones of the filter plate, and selective means for selectively shuttering said color filter means in turn to produce a sequence of color illumination.

* * * * *